United States Patent [19]

Sisk et al.

[11] Patent Number: 5,496,375
[45] Date of Patent: Mar. 5, 1996

[54] PROSTHETIC IMPLANT WITH CIRCUMFERENTIAL POROUS PAD HAVING INTERLOCKING TABS

[75] Inventors: Bruce A. Sisk, Bremen; Alden J. Hartz, South Bend, both of Ind.

[73] Assignee: Zimmer, Inc., Warsaw, Ind.

[21] Appl. No.: 307,982

[22] Filed: Sep. 14, 1994

[51] Int. Cl.⁶ .................................. A61F 2/28; A61F 2/32
[52] U.S. Cl. .................................. 623/16; 623/23
[58] Field of Search .................. 623/1, 11, 12, 623/16, 18, 19, 22, 23

[56] References Cited

U.S. PATENT DOCUMENTS

| | | | |
|---|---|---|---|
| 3,906,550 | 9/1975 | Rostoker et al. | 3/1.912 |
| 4,064,567 | 12/1977 | Burstein et al. | 3/1.91 |
| 4,167,992 | 9/1979 | McClellan | 188/322 |
| 4,479,271 | 10/1984 | Bolesky et al. | 3/1.911 |
| 4,570,271 | 2/1986 | Sump | 623/18 |
| 4,589,883 | 5/1986 | Kenna | 623/22 |
| 4,636,219 | 1/1987 | Pratt et al. | 623/22 |
| 4,644,942 | 2/1987 | Sump | 623/16 |
| 4,718,914 | 1/1988 | Frey et al. | 623/16 |
| 4,718,916 | 1/1988 | Morscher | 623/23 |
| 4,728,335 | 3/1988 | Jurgutis | 623/23 |
| 4,734,971 | 4/1988 | Dupasquier | 29/417 |
| 4,828,566 | 5/1989 | Griss | 623/23 |
| 5,013,324 | 5/1991 | Zolman et al. | 623/23 |
| 5,018,285 | 5/1991 | Zolman et al. | 29/465 |

FOREIGN PATENT DOCUMENTS

| | | | |
|---|---|---|---|
| 0178650A2 | 4/1986 | European Pat. Off. | A61F 2/30 |
| 0273871A1 | 7/1988 | European Pat. Off. | A61F 2/36 |
| 2404214 | 8/1974 | Netherlands | A61F 1/00 |

*Primary Examiner*—David Isabella
*Attorney, Agent, or Firm*—Margaret L. Geringer

[57] ABSTRACT

The present invention provides a prosthetic implant 510 including a stem portion 520 having a discrete, circumferential porous pad 526 mounted directly on the stem portion 520 in surrounding relation thereto. The pad 526 includes a first end 528 and a second end 529 such that when the pad 526 is mounted on the stem portion 520, the first end 528 and the second end 529 face each other and are interconnected at a seam 527 therebetween, such that the interconnection reduces the advancement of wear debris along the seam 527.

The interconnection may include at least one pair of mating interlocking tabs 600 on the pad 526. Alternatively, the improved interconnected seam 700 may be improved by the use of a metallurgical bond along the seam 727 or by the use of a filler material along the seam 727 to reduce the possibility of wear debris advancing or traveling along the seam.

5 Claims, 2 Drawing Sheets

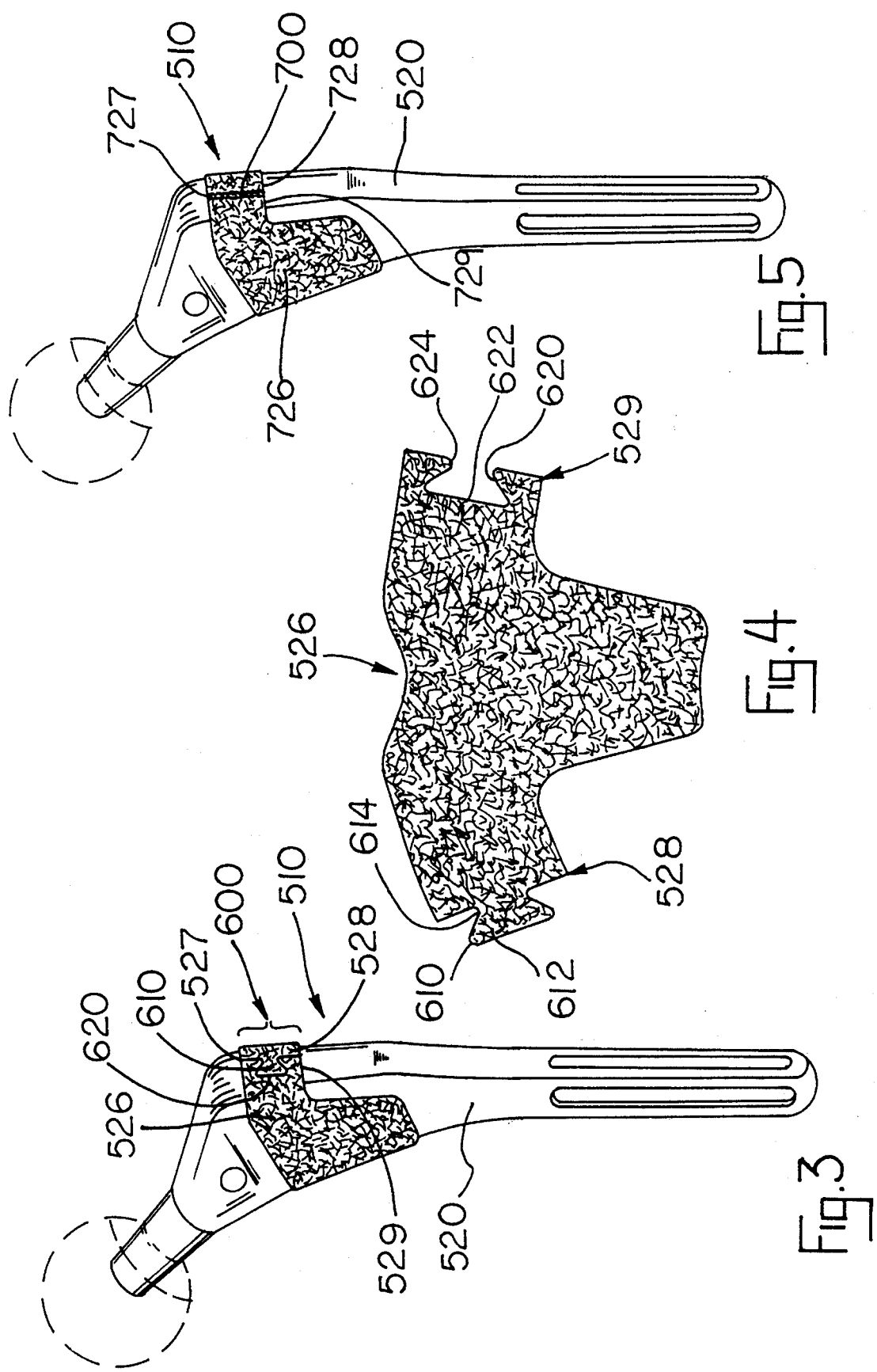

5,496,375

PROSTHETIC IMPLANT WITH CIRCUMFERENTIAL POROUS PAD HAVING INTERLOCKING TABS

FIELD OF INVENTION

The present invention relates to a prosthetic implant and more particularly to such implants including porous surfaces thereon.

BACKGROUND OF THE INVENTION

U.S. Pat. No. 5,013,324 to Zolman et al. discloses a prosthetic implant which includes a discrete, circumferential porous pad mounted directly onto the stem of an implant. The pad includes a first end and a second end such that when the pad is mounted on the stem, the first end and second end of the pad face each other and are flush with one another. This prior art device of U.S. Pat. No. 5,013,324 is shown in FIGS. 1–2 of the present application. The first end and second end of the prior art porous pad shown in FIG. 2 include straight edges which abut each other as shown in FIG. 1 to form a straight seam therebetween.

It has been discovered that over time particulate matter or wear debris may be generated from a prosthetic implant device. This wear debris could travel along this seam in which the two ends of the pad are merely aligned with or abutted against each other. This wear debris could cause bone lysis.

SUMMARY OF THE INVENTION

The present invention provides a prosthetic implant including a stem portion having a discrete, circumferential porous pad mounted directly on the stem portion in surrounding relation thereto. The pad includes a first end and a second end such that when the pad is mounted on the stem portion, the first end and the second end face each other and are interconnected at a seam therebetween, such that the interconnection reduces the advancement of wear debris along seam.

This interconnection may include at least one pair of mating interlocking tabs on the pad. Alternatively, the interconnection may be improved by the use of a metallurgical bond along the seam or by the use of a filler material along the seam to reduce the possibility of wear debris advancing or traveling along the seam.

Accordingly, it is an advantage of the invention to provide an improved interconnection for a discrete porous pad for an implant which reduces the possibility of wear debris advancing or traveling along the seam.

Another advantage of the invention is to provide an improved interconnection of the first and second ends of the porous pad.

A further object of the invention is to provide interlocking tabs for securing the interconnection of the pad ends.

Still other advantages of the invention will become apparent upon reference to the accompanying drawings.

BRIEF DESCRIPTION OF THE DRAWINGS

FIG. 3 is a perspective view of a hip prosthesis according to the present invention.

FIG. 4 is a plan view of the porous pad for the hip prosthesis of FIG. 3.

FIG. 5 is a perspective view of a hip prosthesis illustrating an alternate embodiment of the porous pad.

DESCRIPTION OF THE PREFERRED EMBODIMENT

Figure 2:
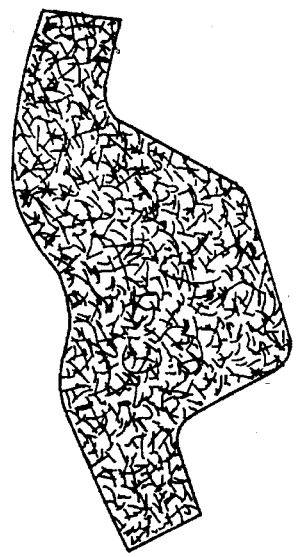
FIG. 2 is a plan view of the prior art porous pad for the hip prosthesis of FIG. 1.
Figure 1:
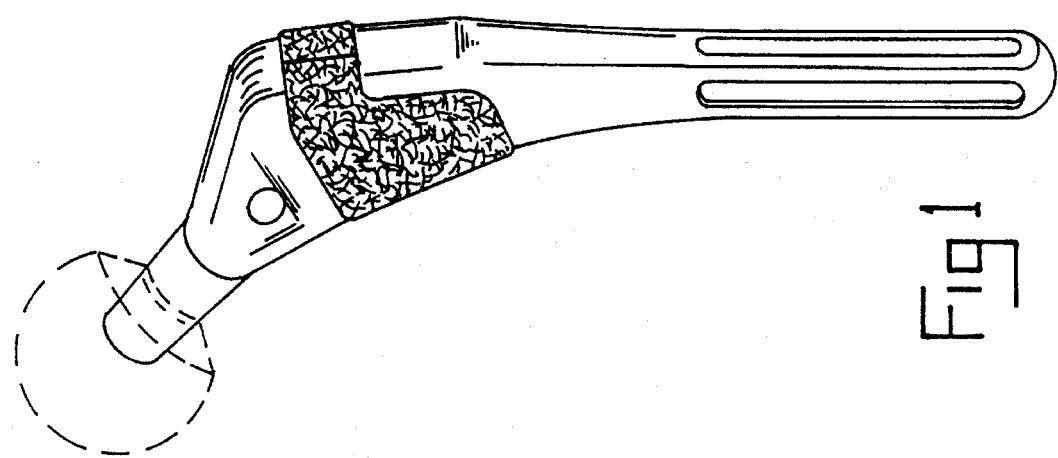
FIG. 1 is a perspective view of the prior art hip prosthesis of U.S. Pat. No. 5,013,324.

The preferred embodiment described herein is not intended to be exhaustive or to limit the invention to the precise form disclosed. Rather, it is chosen and described to best explain the invention so that others skilled in the art might utilize its teachings.

It is noted that U.S. Pat. No. 5,013,324 is incorporated herein by reference.

FIGS. 3–4 illustrate a particularly advantageous embodiment of a prosthetic implant according to the present invention. The invention will be described with reference to a femoral component 510 of a hip prosthesis, and is particularly suitable as such. However, it is understood that the principles of the invention may be suitable for other implants having elongated fixation stems.

The prosthetic implant 510 includes a stem portion 520 having a discrete, circumferential porous pad 526 mounted directly on the stem portion 520 in surrounding relation thereto. The pad 526 includes a first end 528 and a second end 529 such that when the pad 526 is mounted on the stem portion 520, the first end 528 and the second end 529 face each other and are interconnected at a seam 527 therebetween such that the interconnection reduces the advancement of wear debris along the seam 527.

The interconnection for reducing the advancement of wear debris may include at least one pair of mating interlocking tabs 600 on the pad 526. The at least one pair of tabs 600 includes a first protruding tab member 610 extending from the first end 528 of the pad 526 and a first recessed portion 620 extending into the second end 529 of the pad 526. The first recessed portion 620 corresponds to and interlocks with the first tab member 610. The first protruding tab 610 includes an enlarged tab portion 612 and a narrower tab portion 614 interconnecting the tab 610 to the first end 528 of the pad 526. The first recessed portion 620 includes a corresponding enlarged recess portion 622 and narrower recess portion 624 to matingly interfit with the first tab 610.

The interlocking tab arrangement 600 helps to reduce the advancement of wear debris along the seam 527 by providing a more convoluted path of travel, thus inhibiting the advancement of wear debris. While the embodiment shown in FIGS. 3–4 discloses a single pair of interlocking tabs 600, it is noted that a plurality of such interlocking tabs may be provided, as desired.

The pad 526 may be of any suitable size and shape to accommodate the geometry of different shaped parts, as well as different sizes of components. The actual shape of the pair of interconnecting tabs 600 may also vary, as desired.

The pad 526 is preferably formed of a fiber metal material, and may be formed and applied to the stem portion 520 as described in U.S. Pat. No. 5,013,324. However, any suitable method of forming the pad 526 and applying the pad 526 to the stem portion 520 to secure the pad 526 to stem 520 may be utilized. The pad may be metallurgically bonded to stem 520 or secured by any other suitable attachment means or bonding material.

The pair of interlocking tabs 600 not only provides an interlocked joint which will reduce the possibility of wear debris from traveling through the bone canal, but this interlocked joint also helps ensure a proper fit of mating pad portions which in turn holds the pad 526 securely to the stem 520 to assist when bonding the pad 526 to the stem 520.

An alternate embodiment is shown in FIG. 5 in which porous pad 726 includes first end 728 which aligns with second end 729 at seam 727. Although the seam 727 may be straight, as shown in FIG. 5, the seam 727 is improved by providing an interconnected seam 700. The interconnected seam 700 may be provided by utilizing a metallurgical bond along seam 727 or by providing a filler material along the seam. This interconnected seam 700 helps reduce the advancement of wear debris along seam 727 by closing off the seam 727.

The metallurgical bonding may utilize a suitable filler metal for welding the first and second ends 728 and 729 together. Alternately, any suitable filler material may be applied along the seam, such as a suitable plastic or other filler material in order to close up any gap or path between ends 728 and 729, thus reducing the possibility for the advancement of wear debris passing through or along the seam 727. Such improved interconnected seam or filler material may also be utilized in conjunction with the interconnecting tabs 600 in the embodiment of FIG. 3.

While this invention has been described in terms of a particularly advantageous embodiment, those skilled in the art can appreciate that modifications can be made without departing from the spirit and scope of this invention.

We claim:

1. A prosthetic implant including a stem portion having a discrete, circumferential porous pad mounted directly on the stem portion in surrounding relation thereto, the pad includes a first end and a second end such that when the pad is mounted on the stem portion, the first end and the second end face each other and are interconnected at a seam therebetween by a means for reducing the advancement of wear debris along the seam, and wherein the means for reducing the advancement of wear debris includes at least one pair of mating interlocking tabs on the pad, wherein the at least one pair of tabs includes a first protruding tab member extending from the first end of the pad and a first recessed portion extending into the second end of the pad, said first recessed portion corresponding to and interlocking with the first tab member.

2. The implant of claim 1 wherein the first protruding tab includes an enlarged tab portion and a narrower tab portion interconnecting the tab to the first end of the pad and wherein the first recessed portion includes a corresponding enlarged recess portion and narrower recess portion to matingly interfit with the first tab.

3. A prosthetic implant including a stem portion having a discrete, circumferential porous pad mounted directly on the stem portion in surrounding relation thereto, the pad includes a first end and a second end such that when the pad is mounted on the stem portion, the first end and the second end face each other and are interconnected of a seam by at least one pair of mating interlocking tabs on the pad, wherein the at least one pair of tabs includes a first protruding tab member extending from the first end of the pad and a first recessed portion extending into the second end of the pad, said first recessed portion corresponding to and interlocking with the first tab member for reducing the advancement of wear debris along the seam.

4. The implant of claim 3 wherein the first protruding tab includes an enlarged tab portion and a narrower tab portion interconnecting the tab to the first end of the pad and wherein the first recessed portion includes a corresponding enlarged recess portion and narrower recess portion to matingly interfit with the first tab.

5. A method of reducing the advancement of wear debris in a prosthetic implant comprising the steps of:

a) providing the implant with a stem portion;

b) providing a discrete circumferential porous pad having a first end and a second end;

c) mounting the pad directly on the stem portion in surrounding relation thereto, so that the first end and the second end face each other; and d) interconnecting the first end and second end at a seam therebetween to provide a means for reducing the advancement of wear debris along the seam, and wherein the interconnecting step further includes providing at least one pair of mating interlocking tabs on the pad.

* * * * *